United States Patent [19]

Squire

[11] Patent Number: 4,560,778

[45] Date of Patent: Dec. 24, 1985

[54] OLIGOMERS OF PERFLUORO(2,2-DIMETHYL-1,3-DIOXOLE) AND THEIR FLUORINATION PRODUCTS

[75] Inventor: Edward N. Squire, Glen Mills, Pa.

[73] Assignee: E. I. Du Pont de Nemours and Company, Wilmington, Del.

[21] Appl. No.: 650,865

[22] Filed: Sep. 14, 1984

Related U.S. Application Data

[62] Division of Ser. No. 421,825, Sep. 23, 1982, Pat. No. 4,496,749, which is a division of Ser. No. 279,867, Jul. 2, 1981, Pat. No. 4,409,393.

[51] Int. Cl.$^4$ ............................................. C07D 317/00
[52] U.S. Cl. ..................................... 549/455; 528/402
[58] Field of Search ......................... 549/455; 526/427

[56] References Cited

U.S. PATENT DOCUMENTS

| | | | |
|---|---|---|---|
| 3,316,216 | 4/1967 | Fawcett et al. | 525/471 |
| 3,865,845 | 2/1975 | Resnick | 549/455 |
| 3,978,030 | 8/1976 | Resnick | 526/247 |
| 4,399,264 | 8/1983 | Squire | 526/247 |
| 4,431,786 | 2/1984 | Squire | 526/247 |
| 4,485,250 | 11/1984 | Squire | 549/455 |

Primary Examiner—Ethel G. Love
Attorney, Agent, or Firm—Paul R. Steyermark

[57] ABSTRACT

Perfluoro(2,2-dimethyl-1,3-dioxole) forms oligomers on standing in the presence of an ether. The preferred ethers are aliphatic and cycloaliphatic, especially tetrahydrofuran. Free radical generators, especially peroxydicarbonates, may be added to the reaction medium. The oligomers have a degree of polymerization of about 2-8. They are useful as lubricants, hydraulic fluids, heat transfer agents, and plasticizers, and as intermediates to oligomeric acid fluorides and acids, which acids are useful surfactants.

6 Claims, No Drawings

OLIGOMERS OF PERFLUORO(2,2-DIMETHYL-1,3-DIOXOLE) AND THEIR FLUORINATION PRODUCTS

CROSS-REFERENCE TO RELATED APPLICATION

This is a divisional of my application Ser. No. 4,221,825, filed Sept. 23, 1982, now U.S. Pat. No. 4,496,749 which was a divisional of application Ser. No. 279,867, filed July 2, 1981, now U.S. Pat. No. 4,409,393, granted Oct. 11, 1983.

BACKGROUND OF THE INVENTION

This invention relates to a process for making oligomers of perfluoro(2,2-dimethyl-1,3-dioxole), which are useful as lubricants, hydraulic fluids, heat transfer fluids, and plasticizers, and as intermediates for making certain perfluoroacids and acid fluorides.

U.S. Pat. No. 3,978,030 to Resnick discloses solid polymers of perfluoro(2,2-dimethyl-1,3-dioxole). The preparation of perfluoro(2,2-dimethyl-1,3-dioxole), sometimes abbreviated hereinafter to PDD, also is described in the above patent. PDD has the following formula (1)

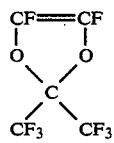  (1)

Solid polymers were obtained on standing at room temperature in a dry box as well as on irradiation with ultraviolet light. No low molecular weight oligomers of PDD have been reported, however.

SUMMARY OF THE INVENTION

There is now provided a process for making oligomers of perfluoro(2,2-dimethyl-1,3-dioxole), said process comprising allowing perfluoro(2,2-dimethyl-1,3-dioxole) to stand in the presence of an ether, then recovering the oligomer from the ether solution.

DETAILED DESCRIPTION OF THE INVENTION

The oligomers of the present invention form at temperatures as low as $-5°$ C. or even lower or as high as 70° C. or so. Although the oligomerization is faster at higher temperatures, it is a slow reaction, which may take days, weeks, or months at $-5°$ C. Since PDD boils at 33° C., it is recommended that oligomerization above 60° C. be carried out in pressure equipment.

Aliphatic and cycloaliphatic ethers are preferred because in their presence the highest conversions are obtained. Representative ethers which can be used to make the oligomers of this invention include: methyl, ethyl, propyl and isopropyl, and butyl ethers; tetrahydrofuran; dioxane, and dioxolane; methylal, diethyl acetal, and dimethyl heptal; and polymeric ethers such as polyethylene oxide, polypropylene oxide, and acetals of polyvinyl alcohol. It is not necessary to purify the ether to remove ether peroxides which usually are present therein.

The normal way of carrying out this oligomerization is to dissolve PDD in the ether and let the solution stand at the desired temperature for a period of at least several hours, then distill off any unchanged PDD and the ether. The oligomer product is found in the heel (residue) of the distillation. It has been found practical to also have water present in the oligomerization medium. The volume of water may thus vary from zero to about twice the volume of the ether, the latter being about one to three times the volume of PDD. However, neither the presence of water nor the above-recited volume proportions are critical to the success of this invention.

The preferred ether is tetrahydrofuran because in its presence the oligomerization proceeds relatively quickly; it is miscible with water; and it has a low boiling point of 65°–66° C. which permits easy removal by distillation.

It is often advantageous to add an initiator to the reaction. The initiator can be any free radical generator known to the art. Many free radical generators are commercially available. They usually are peroxy, peroxycarbonyl, or azo compounds. The proper choice will depend, among others, on the initiator's decomposition temperature at which free radical generation takes place. The preferred initiators will rapidly generate free radicals at about 50°–65° C. Those having lower decomposition temperatures may present a safety hazard. The particular class of initiators preferred in the process of this invention are peroxydicarbonates such as, for example, bis(4-t-butylcyclohexyl)peroxydicarbonate.

This oligomerization reaction being free radical-initiated and terminated, the oligomers will contain groups derived from the free radical molecule. Aliphatic and cycloaliphatic ethers react readily with PDD, so that at least a portion of all the PDD oligomers formed in the reaction will contain ether residues. The oligomers of this invention can be shown by instrumental methods such as infrared and nuclear magnetic resonance spectroscopy to form chains comprised of PDD units joined through double bonds as shown below in Formula (2),

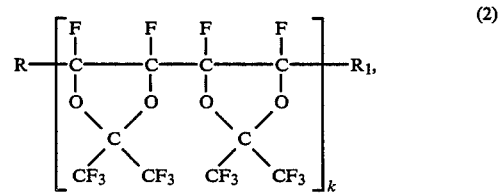  (2)

where k is about 1–4 but usually is at least 2. R and $R_1$ are fragments of the radical causing oligmer chain initiation and termination. Each of R and $R_1$ can thus be hydrogen or an ether residue; or, it can be a group derived from any initiator present. The R and $R_1$ groups do not necessarily have to be always located at the ends of the oligomer molecule but may be isnide the molecule. Thus, when the oligomerization is carried out in the presence of tetrahydrofuran, oligomers having the following structures (3) and (4) may be formed:

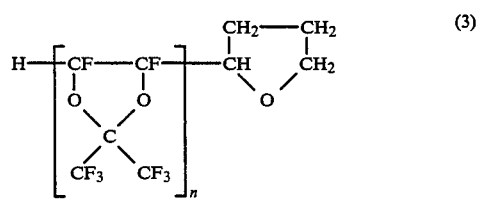  (3)

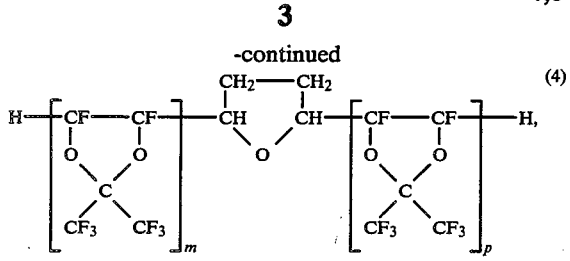

where n is about 2–8, while each of m and p is about 1–4 but usually at least 2, and the average degree of oligomerization of products (3) and (4) is about the same; so that for the purpose of this disclosure in structures (3) and (4) m+p≈n.

The upper limit of n in most oligomers will be 4 to 6. At the upper end of the n range, the oligomers will be very viscous liquids or low-melting noncrystalline solids (waxes) incapable of being pressed into self-supporting films. Where n is a low number, the oligomer is a mobile liquid.

Fluorination of the oligomers of the present invention with elemental fluorine may lead to perfluoracid fluorides or perfluoroacids. Thus, an oligomer of formula (3), above, gives a product of both fluorination and cleavage, which has the following structure (5):

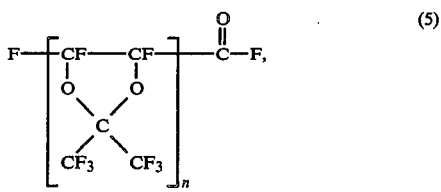

which can be readily hydrolyzed by a mild base to the corresponding perfluoroacid salt, e.g., (6)

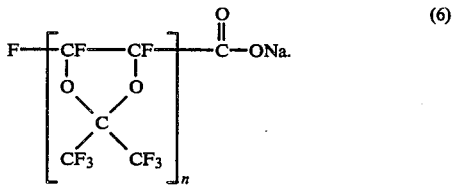

Acids and salts such as 6 are useful surfactants for fluoromonomers in emulsion polymerization reactions. Acid fluorides (5) undergo the usual reactions of acid fluorides, including addition in the presence of fluoride ions to hexafluoropropylene oxide.

This invention is now illusstrated by the following examples.

Preparation of PDD

PDD was prepared in several runs by dechlorination of perfluoro-2,2-dimethyl-4,5-dichloro-1,3-dioxolane with magnesium turnings in the presence of mercuric chloride and iodine. The addition of mercuric chloride was an improvement over Example 2 of U.S. Pat. No. 3,978,030 to Resnick. As in that example, tetrahydrofuran was used as the reaction solvent. The amount of tetrahydrofuran was 80 cm³ (about 71 g) per 18.9 g of the dioxolane. The amounts of the other ingredients were as follows: magnesium 7.3 g, mercuric chloride 0.2 g, and iodine 0.1 g. In each run about 15 cm³ of crude product distilling between about 33° and 66° C. was collected. This consisted mainly of tetrahydrofuran and a smaller proportion of PDD.

Oligomerization of PDD (A) The distillates of two runs were combined, mixed with 50 cm³ of water, and placed overnight in a refrigerator at about 0° C. The PDD, which settled to the bottom, was separated, mixed with 25 cm³ of water, and returned to the refrigerator. This water extraction process to remove the tetrahydrofuran was carried out twice more during a course of two months. The organic material was stored for 3 months at −5° C. and then was distilled. The distillate was unchanged PDD, boiling at about 33° C., but a high boiling heel remained. It was identified by infrared and nuclear magnetic resonance spectroscopy and by gas chromatography to be a mixture of PDD oligomers.

(B) The preparation of PDD oligomers was repeated by keeping a PDD-tetrahydrofuran-water mixture at temperatures varying from −5° to 66° C. for periods of days or hours (the reaction requiring less time at higher temperatures). The degree of PDD conversion into oligomers was about 20%. The recurring PDD structure was confirmed by nuclear magnetic resonance spectroscopy. This technique also indicated the presence of CH bonds in the molecule.

The average degree of oligomerization of liquid products was about 4 (n=4), as determined by nuclear magnetic resonance. Occasionally, very viscous or even waxy solid products were obtained. Their degree of oligomerization, n, was at least about 6.

(C) A small bottle was charged with 4 g of PDD, 5 g of diethyl ether, and 0.01 g of bis(4-t-butylcyclohexyl)-peroxydicarbonate and allowed to stand at room temperature for one week. Evaporation of the ether left a clear, colorless, oily residue. Its infrared spectrum was consistent with that of an oligomer having recurring PDD units joined through C—F bonds. The spectrum also had bands characteristic of C—H bonds in radicals arising from diethyl ether. A portion of the oligomeric material was soluble in diethyl ether.

(D) A solution of 4 g of PDD and 0.01 g bis(4-t-butyl-cyclohexyl)peroxydicarbonate in 5 g of tetrahydrofuran was allowed to stand at room temperature for one week. Evaporation of tetrahydrofuran left a clear, colorless oil. The infrared spectrum of this oil contained bands consistent with the recurring PDD structure as well as some bands that could be attributed to C—H end groups.

Fluorination of PDD Oligomer—Preparation of Oligomeric Carboxylic Acid

An oligomer mixture, 2.4 g (from the reaction of PDD and tetrahydrofuran) and 50 g of 1,1,2-trichloro-1,2,2-trifluoroethane were charged into a 350 cm³ shaker tube which was cooled, evacuated, and pressured at −30° C. to 1.19 MPa with a mixture of 25 vol. % of fluorine and 75 vol. % of nitrogen. The tube was agitated, gradually heated to 180° C. over a four hour period, and then cooled.

The resulting solution was mixed well with a solution of 6 g of potassium carbonate in 20 cm³ of water. The organic phase was separated from the water layer, and the solvent was distilled off leaving behind solid, white potassium salts of the oligomeric carboxylic acids. Identification of the salts was by the relatively intense infrared absorbance in the region of 5.9 μm (—COO⁻) and the similarity of the other parts of the IR scan to the absorption of the original PDD oligomer, especially the strong bands in the regions of 7.6, 8.0, 8.7, 9.1, 10.1 and 13.8 μm; bands attributable to carbon-hydrogen bonds were absent. Elemental analysis gave C, 22.41, 22.16 and F, 52.29, 52.23%, which is consistent with a PDD oligomer having four dioxolane rings and terminated by two-COOK groups, one at each end.

The water solution, which upon standing had gelled, was made strongly acidic by the addition of hydrochloric acid. The aqueous solution was then extracted with 1,1,2-trichloro-1,2,2-trifluoroethane; evaporation of the solvent gave the liquid carboxylic acids which were identified by infrared absorbance spectroscopy. The scan showed strong absorbancies in the regions of 3.2 μm (—OH) and 5.8 μm (CO), corresponding to those of carboxylic acids, as well as absorbancies attributable to the PDD rings. NMR analysis showed that the average oligomeric carboxylic acid contained 4 recurring PDD units. Since the fluorination cleaves the oligomer at the ether sites the average oligomer prior to fluorination contained at least 4 PDD units.

Fluorination of PDD Oligomer—Preparation of Oligomeric Acid Fluorides

A PDD oligomeric mixture, 2.4 g, and 50 g of 1,1,2-trichloro-1,2,2-trifluoroethane were charged into a 350 ml stainless steel shaker tube; the tube was cooled, evacuated and charged at −25° C. with a mixture of 25 vol. % fluorine and 75 vol. % nitrogen at a pressure of 1.16 MPa. The tube was agitated and slowly warmed to room temperature and finally heated to 180° C. After cooling, the solution was discharged from the tube and the solvent was distilled off, leaving 2.0 g of liquid acid fluorides. The oligomeric acid fluorides were identified by their infrared absorption peak in the region of 5.3 m in addition to the typical PDD oligomer absorbancies. During the handling of the acid fluoride some hydrolysis occurred, resulting in the formation of some carboxylic acid groups as evidenced by absorbance in the region of 5.6 μm.

I claim:

1. A method of oligomerizing perfluoro(2,2-dimethyl-1,3-dioxole), said method consisting in maintaining perfluoro(2,2-dimethyl-1,3-dioxole) in contact with an organic ether selected from the class consisting of liquid aliphatic and cycloaliphatic, monomeric and polymeric ethers for a sufficient period to cause formation of a liquid or waxy, noncrystalline oligomer incapable of being pressed into a self-supporting film.

2. The method of claim 1 wherein the organic ether is tetrahydrofuran.

3. The method of claim 2 wherein perfluoro(2,2-dimethyl-1,3-dioxole) and tetrahydrofuran are maintained in contact with each other at a temperature of about −5° C. to 70° C. for a period of several hours to several months.

4. The method of claim 3 wherein water also is present in the oligomerization reaction.

5. A method of claim 1 wherein a free radical generator also is added to the oligomerization reaction.

6. The method of claim 5 wherein the free radical generator is a peroxydicarbonate.

* * * * *